(12) United States Patent
Devlin (10) Patent No.: US 12,011,343 B2
(45) Date of Patent: Jun. 18, 2024

(54) SKIN FISSURE MITIGATION SYSTEM (71) Applicant: Maureen Devlin, Seattle, WA (US)

(72) Inventor: Maureen Devlin, Seattle, WA (US)

(73) Assignee: Maureen Devlin, Seattle, WA (US)

( * ) Notice: Subject to any disclaimer, the term of this patent is extended or adjusted under 35 U.S.C. 154(b) by 338 days.

(21) Appl. No.: 17/349,820

(22) Filed: Jun. 16, 2021

(65) Prior Publication Data

US 2022/0401268 A1 Dec. 22, 2022

(51) Int. Cl.
A61F 13/00 (2024.01)
A61F 13/06 (2006.01)

(52) U.S. Cl.
CPC .................................. A61F 13/067 (2013.01)

(58) Field of Classification Search
None
See application file for complete search history.

(56) References Cited

U.S. PATENT DOCUMENTS

| 3,584,622 | A | * | 6/1971 | Domenico | A61F 13/066 |
| | | | | | 602/65 |
| 5,827,213 | A | * | 10/1998 | Jensen | A61F 13/101 |
| | | | | | 128/889 |
| 6,629,945 | B1 | * | 10/2003 | Stromgren | A61F 13/067 |
| | | | | | 602/5 |
| 7,049,478 | B1 | * | 5/2006 | Smith | A61F 13/067 |
| | | | | | 128/892 |
| 7,091,394 | B2 | * | 8/2006 | Kolte | A61F 13/0203 |
| | | | | | 602/42 |
| 9,603,596 | B2 | | 3/2017 | Riskin et al. | |
| 10,398,802 | B2 | | 9/2019 | Jonn et al. | |
| 11,395,766 | B2 | * | 7/2022 | Leppänen | A61F 13/064 |
| 2010/0130946 | A1 | * | 5/2010 | Medley | A61M 35/10 |
| | | | | | 604/293 |
| 2016/0135946 | A1 | | 5/2016 | Aoki et al. | |
| 2016/0199232 | A1 | * | 7/2016 | Stakes | A61F 13/00085 |
| | | | | | 604/308 |
| 2018/0303483 | A1 | | 10/2018 | Zhang | |
| 2020/0093647 | A1 | * | 3/2020 | McClendon | A61M 35/00 |

(Continued)

FOREIGN PATENT DOCUMENTS

| FR | 2977149 A1 | * | 1/2013 | ......... A61F 13/0206 |
| GB | 2263236 A | * | 7/1993 | ........... A61F 13/069 |
| KR | 101949608 B1 | * | 2/2019 | ....... A61F 13/00017 |

OTHER PUBLICATIONS

KR 101949608 B1Translation, Feb. 19, 2019. (Year: 2019).*

(Continued)

Primary Examiner — Kim M Lewis
(74) Attorney, Agent, or Firm — Seed IP Law Group LLP (57) ABSTRACT A skin fissure mitigation device includes a base and a sidewall coupled to the base in a concave arrangement to define a cavity structured to receive a heel of a foot of a user. The device includes an adhesive on a surface of the base or sidewall or both facing the heel of the foot of the user to adhere the device to the foot of the user. At least one of the base and the sidewall include an elastic material structured to apply tension to a bottom surface of the foot of the user to close skin fissures on the bottom surface of the foot of the user. The base and sidewall may also include tabs for increasing the tension in the device.

12 Claims, 6 Drawing Sheets (56) References Cited

U.S. PATENT DOCUMENTS

2022/0257425 A1\* 8/2022 Berry .................. A61F 13/067

OTHER PUBLICATIONS

FR 2977149 A1 translation (Year: 2013).\*
"It's here!" Screen capture of Heal a Heel Facebook post dated Jun. 9, 2020, <https://www.facebook.com/healaheel/videos/917043462092414>, 1 page.
"Smooth heals this weekend? YES!" Screen capture of Heal a Heel Instagram post dated Jun. 26, 2020, <https://www.instagram.com/p/CNYJaqLh5CL/>, 1 page.
"Soft smooth heels are only a weekend away," Screen capture of Heal a Heel Instagram post dated Apr. 7, 2021, <https://www.instagram.com/p/CNYJaqLh5CL/>, 1 page.

\* cited by examiner

SKIN FISSURE MITIGATION SYSTEM

BACKGROUND

Technical Field

The present disclosure relates to devices and methods for mitigation of skin fissures, and more particularly, to devices and methods for applying tension to skin fissures.

Description of the Related Art

Cracks or skin fissures in the heel or on the bottom of a user's foot are a known health issue. Skin on the heel or on the bottom of the foot can crack when the skin becomes dry and thick and experiences increased pressure from the pad under the skin. This issue can be caused by genetic and environmental factors, such as relative humidity and the style of footwear commonly worn by the user.

In response, certain products have been developed that try to address skin fissures in the heel or foot area. For example, certain creams and lotions are marketed for healing skin fissures in the heel or foot area. Such creams or lotions typically do not address or improve severe cases of skin fissures and thus are not suitable for a wide range of users. Further, creams and lotions can be absorbed by socks or shoes of the user, which limits their effectiveness and may also cause damage or staining to the socks or shoes. While wraps have also been proposed to address skin fissures, such wraps have an unsightly appearance when the user is in public because they are visible outside of the user's shoes and socks in many cases and particularly on the top of the foot near the ankle. Some wraps and tapes also cause further skin irritation, especially if creases or folds form in the wrap or tape during application. Moreover, known wraps and tapes are thick and bulky and may interfere with the use or fit of shoes and socks while the user is wearing the wrap or tape.

BRIEF SUMMARY

The present disclosure is generally directed to devices, systems, and methods for the mitigation of skin fissures or cracks proximate a heel of a user, such as on the bottom, sides, or crown of the foot in the heel area. The device is structured to engage the heel of the user and provide tension to the skin at the heel and thereby facilitate closing the fissures, allowing them to heal naturally. The stress on the skin of the heel area when walking and engaging in other activities is a cause of the fissures, and countering this stress on the skin of the heel area with the disclosed skin fissure mitigation system helps enables the skin to heel. Further, the skin fissure mitigation devices and methods are designed to be comfortably worn beneath a user's socks and shoes, while not being visible in most types of footwear.

One or more embodiments of a device structured to engage a heel of a foot of a user may be summarized as including: a base; a sidewall coupled to the base; a cavity defined by the base and the sidewall, the cavity structured to receive the heel of the foot of the user; and an adhesive on at least a portion of the base and least a portion of the sidewall, wherein at least one of the base and the sidewall include an elastic material structured to apply tension to the foot of the user.

The device may further include: the base and the sidewall being a single, continuous, integral layer of material including the elastic material; the base having a first surface facing the foot of the foot of the user and a second surface opposite the first surface, the adhesive on the first surface of the base; the sidewall having a first surface facing the heel of the foot of the user and a second surface opposite the first surface, the adhesive on the first surface of the sidewall; a plurality of tabs coupled to at least one of the base and the sidewall, the plurality of tabs structured to apply tension to the elastic material; the plurality of tabs including at least three first tabs, each of the at least three first tabs coupled to the sidewall and spaced equidistant from each other along the sidewall; each of the at least three first tabs extending from the sidewall in a vertical direction; and the plurality of tabs including at least one second tab coupled to the base and extending from the base in a horizontal direction.

One or more embodiments of a device structured to apply tension to skin fissures in a bottom surface of a foot of a user may be summarized as including: a layer of elastic material structured to engage the foot of the user, the layer of elastic material having a first surface facing the foot of the user and a second surface opposite the first surface; and a layer of adhesive on the first surface of the layer of elastic material, wherein the layer of elastic material is in tension on the foot of the user to close skin fissures in the bottom surface of the foot of the user.

The device may further include: the layer of elastic material having a concave shape with a base and a sidewall coupled to the base; the sidewall including at least one opening in the sidewall configured to apply tension to the layer of elastic material; a plurality of tabs coupled to the layer of elastic material and extending from the layer of elastic material in a vertical direction; the plurality of tabs being spaced equidistant from each other and each of the plurality of tabs having an identical shape; the sidewall includes a flange that is angled relative to the base and the sidewall and continuously tapering from the sidewall to the base; and the layer of elastic material being flat and planar and structured to engage only the bottom surface of the foot of the user and including a plurality of tabs coupled to the layer of elastic material and structured to engage a heel of the user.

One or more embodiments of a method for applying a skin fissure mitigation device to a bottom surface and a heel surface of a heel of a user may be summarized as including: applying a base of the skin fissure mitigation device to the bottom surface of the heel of the user, including adhering a first adhesive on a surface of the base to the bottom surface of the heel of the user; pulling a sidewall of the skin fissure mitigation device towards the heel surface of the heel of the user, including applying tension to the bottom surface of the heel of the user to close skin fissures in the bottom surface of the heel of the user; adhering a second adhesive on a surface of the sidewall to the heel surface of the user; pulling sides of the sidewall towards the heel surface of the heel of the user; and adhering a third adhesive on the sides of the sidewall to the heel surface of the heel of the user.

The method may further include: pulling the sidewall of the skin fissure mitigation device includes pulling on tabs coupled to the sidewall of the skin fissure mitigation device; pulling sides of the sidewall includes pulling the sides of the sidewall away from the bottom surface of the heel of the user to apply tension to the heel of the user; and before applying the base of the skin fissure mitigation device, removing a cover on the first adhesive, the second adhesive, and the third adhesive.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn are not necessarily intended to convey any information regarding the actual shape of the particular elements, and may have been selected solely for ease of recognition in the drawings.

DETAILED DESCRIPTION

The present disclosure is generally, but not exclusively, directed to skin fissure mitigation systems, devices, and associated methods. The present disclosure describes and illustrates various embodiments of skin fissure mitigation systems for a heel of a foot of a user that are structured to apply tension to close skin fissures in the heel area and allow them to heal naturally, while also having a low profile design that does not interfere with the use of socks or shoes and is not visible while wearing most types of footwear. However, one of ordinary skill in the art will recognize that the illustrated embodiments are examples only and that the concepts discussed herein can be applied to skin fissure mitigation devices for use with other areas or parts of the human body, as well as outside of the skin fissure mitigation context.

Figures 1, 2:
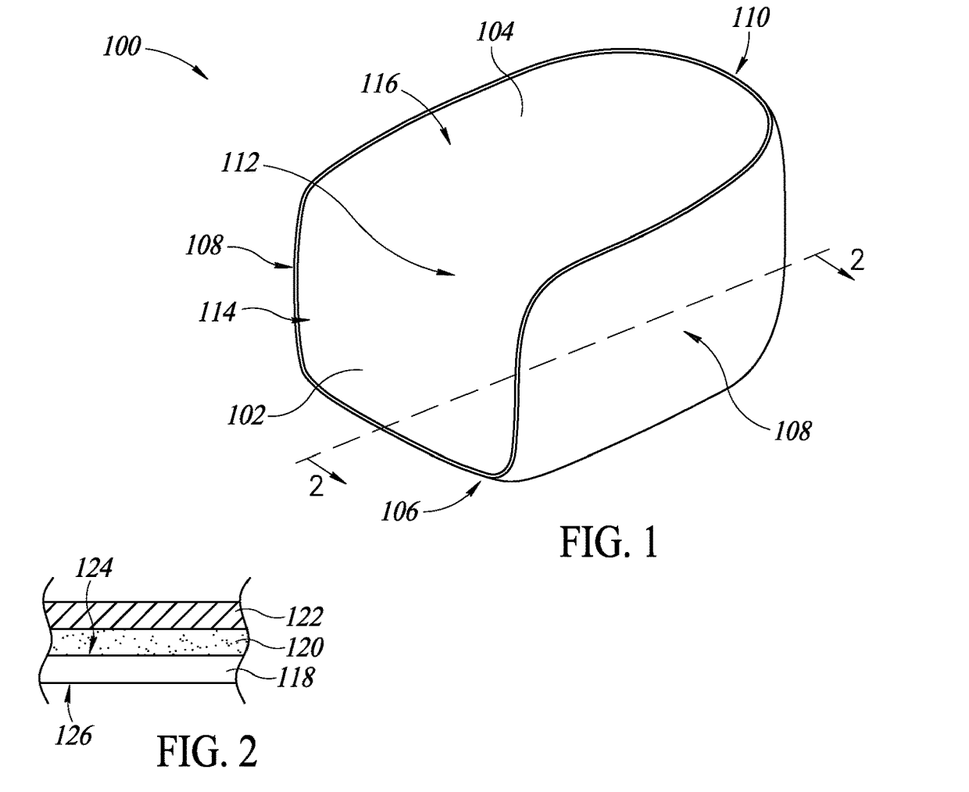
FIG. 1 is an isometric view of an embodiment of a skin fissure mitigation device according to the present disclosure.
FIG. 2 is a detailed cross-sectional view of a portion of the skin fissure mitigation device along line 2-2 in FIG. 1.

FIG. 1 is an isometric view of an embodiment of a skin fissure mitigation device 100 that is structured to engage a heel of a foot of a user. The device includes a base 102 and a sidewall 104 (which may also be referred to herein as a plurality of sidewalls 104) coupled to the base 102. In some embodiments, the base 102 and the sidewall 104 are a single, continuous, integral layer of material with the sidewall 104 generally arranged perpendicular or substantially perpendicular to the base 102. The base 102 is generally flat and planar and is connected to the sidewall 104 by curved transition portions 106. The sidewall 104 also has opposing flat and planar portions 108 connected by a curved portion 110. The base 102 and the sidewall 104 define a cavity 112 that is structured to receive the heel of the foot of the user as well as a first opening 114 and a second opening 116 that are in communication with, or connected to, each other and the cavity 112. The first opening 114 is in a front surface of the device 100 and the second opening is in a top surface of the device 100 such that the openings 114, 116 assist with receiving the heel of the foot of the user. Thus, the device 100 has a concave shape similar to an open-ended channel with at least two sides that are open to an external environment (i.e., a front side and a top side) in order to receive the heel of the foot of the user.

In some embodiments, an entirety of the device 100 is formed from an elastic material. Alternatively, only a portion of the device 100 may be formed from an elastic material with the remaining portions including some other selected and conventional material. In some non-limiting examples, only the base 102 may be formed from elastic material or only the sidewall 104 may be formed from elastic material. Further, only a portion of the base 102 or a portion of the sidewall 104, or both may be formed an elastic material in one or more embodiments. The term "elastic" may refer to a material that stretches up to 100% of its original length (i.e., the length in the stretched configuration is twice the original length). In some non-limiting examples, the elastic material may stretch 1%, 2%, 3%, 4%, 5%, 6%, 7%, 8%, 9%, 10%, 20%, 30%, 40%, 50% or more of its original length in a relaxed, non-stretched configuration. The elastic material may be Nexcare® clear tape manufactured by 3M® as well as various other tapes, films, and adhesives. Further, the elastic material may be polyethylene, polypropylene, rubber, and other like plastics and thermoplastics. The device 100 may be formed by a number of different methods, such as blow molding, injection molding, extrusion molding, laminating, 3D printing, rotational molding, thermoforming, vacuum forming, and other like methods.

In some embodiments, the device 100 is formed from a clear and transparent material so that the device 100 is as inconspicuous as possible and is not obvious to an external observer. Using a clear material may result in less embarrassment for the user and thus an increased likelihood that the user will use the product until the skin fissures are fully healed. However, in some embodiments, the device 100 is formed from a material that is visible and has any selected color, opacity, transparency or other characteristics. While using a clear and transparent material has advantages because it is discrete and may cause less embarrassment, materials with different characteristics, such as those above, may be preferred by some users who wish to match the color of the device 100 with other clothing items or who prefer other material characteristics for aesthetic reasons. Further, the design of the device 100 as a single piece of material or a material that is formed to a shape of a heel, or both, reduces the potential formation of creases or folds during application, and thus reduces the possibility of further irritation by wearing the device 100.

FIG. 2 is a detail view of a portion of the device 100 of FIG. 1 illustrating that the device 100 may further include multiple layers of material in some embodiments. More specifically, the device 100 may include a layer of elastic material 118 with a layer of adhesive 120 on the elastic material 118 and a removable cover layer 122 on the adhesive 120. Thus, in use and as explained further below, a user removes the cover 122 before adhering the device 100 to their foot with the adhesive 120. The layer of elastic material 118 further includes a first surface 124 that faces the heel of the foot of the user in use and a second surface 126 opposite the first surface 124 (i.e., the second surface 126 faces away from the heel of the foot of the user during use).

For clarity, the first surface 124 and the second surface may include the base 102 or the sidewall 104 or both in one or more embodiments.

In some embodiments, the adhesive 120 is only on the first surface 124 and is not on the second surface 126, although the same is not necessarily required. Further, while an entirety of the device 100 may include the layers 118, 120, 122, in some embodiments, only a portion of the device 100 includes all three layers 118, 120, 122. For example, referring back to the discussion above regarding only a portion of the device 100 including an elastic material, the three layers 118, 120, 122 may be present in portions or areas of the device 100 that include the elastic material. Still further, only the base 102 or only the sidewall 104 or portions thereof may include the three layers 118, 120, 122. In one embodiment, there is only one or several strips or areas less than an entire area of the base 102 and the sidewall 104 that includes the layers 118, 120, 122. Thus, the design and layout of the layers 118, 120, 122 can be selected according to various factors, such as desired adhesion strength, material cost, and aesthetics. A combined thickness of the layers 118, 120, 122 may be less than 5 millimeters with the combined thickness of the layers 118, 120 that are applied to the user's heel being less than 3 millimeters. The thickness of the device 100 is an advantage because the device 100 does not interfere with the normal use of socks and shoes and does not inhibit normal activity or range of motion during use.

Figure 3A:
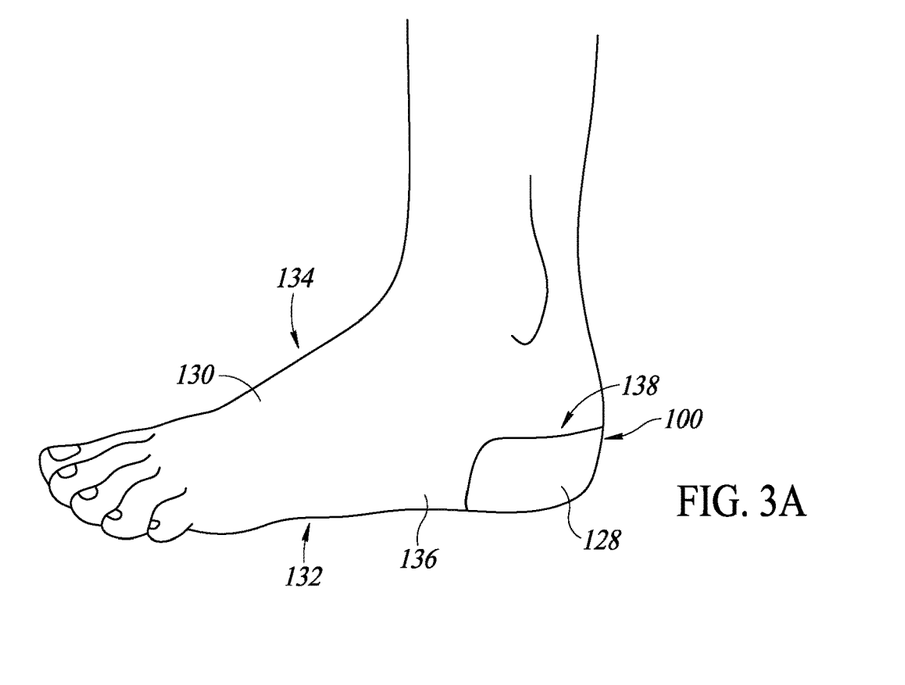
FIGS. 3A-3C are various views of the skin fissure mitigation device of FIG. 1 applied to a heel of a foot of a user.
Figure 3B:
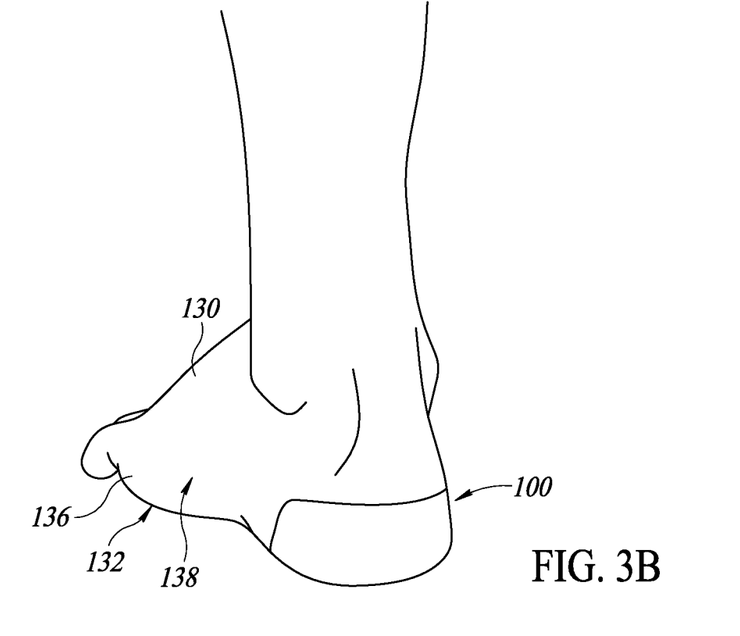
Figure 3C:
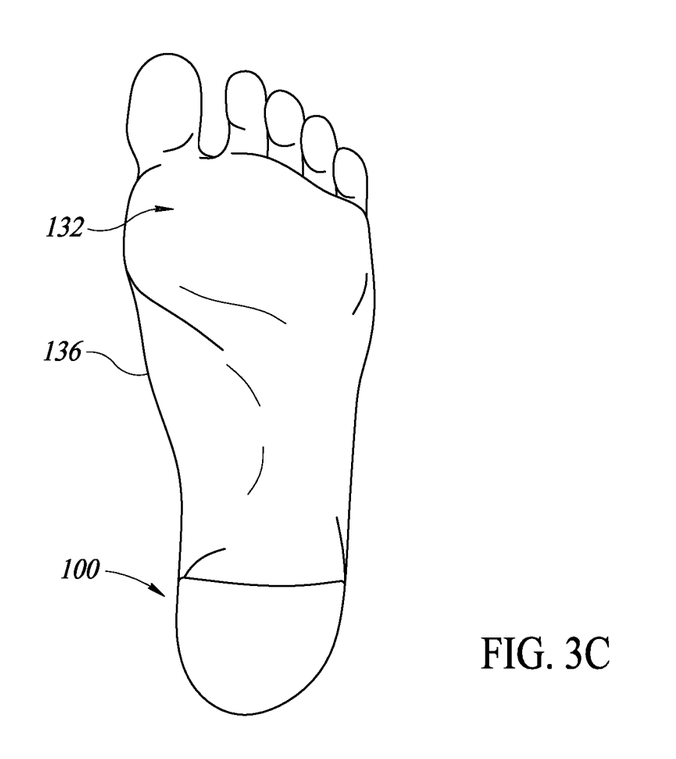

FIGS. 3A-3C are various views of the skin fissure mitigation device 100 applied to a heel 128 of a foot 130 of a user. With reference to FIGS. 3A-3C, the foot 130 of the user includes a bottom surface 132, a top surface 134, a crown 136, and a side surface 138 (which may also be referred to herein as a heel surface 138). In this context only, the crown 136 is the curved area of the foot 130 at the interface between the bottom surface 132 and the side surface 138 of the foot 130. As shown in FIGS. 3A-3C, the device 100 extends around at least a portion of the bottom surface 132, the crown 136, and the side surface 138 of the heel 128 of the foot 130 of the user. In some embodiments, the device 100 does not extend around, contact, or cover any portion of the upper surface 134 of the foot 130 of the user, as best shown in FIG. 3A. As such, one advantage of the device 100 being positioned proximate the heel 128 without extending over the top surface 134 of the foot 130 is that the device 100 allows for socks and shoes to be more easily worn with the device 100 and the device 100 is also not visible when wearing most types of footwear.

Further, the dimensions of the device 100 can be selected according to various factors, such as intended heel fit size in length and in width as well as intended coverage area, among others. In the illustrated embodiment in FIGS. 3A-3C, the device 100 may extend less than 1 inch, 1 inch, 2 inches, 3 inches, 4 inches, 5 inches, 6 inches, 7 inches or more along the bottom surface 132 of the foot 130. Similarly, the device 100 may extend over any of the same range of dimensions along the crown 136 and the side surface 138 of the foot 130 in some embodiments. In one or more embodiments, a length (i.e, front to back) and a height (i.e., top to bottom) of the device 100 are approximately equal such that a length of the bottom surface 132 of the foot 130 covered by the device 100 is approximately equal to a length of the crown 136 and side surface 138 of the foot 100 covered by the device 100. In some embodiments, the length and height are different and may be selected according to design factors, such as desired adhesion strength and intended coverage area.

Figure 4A:
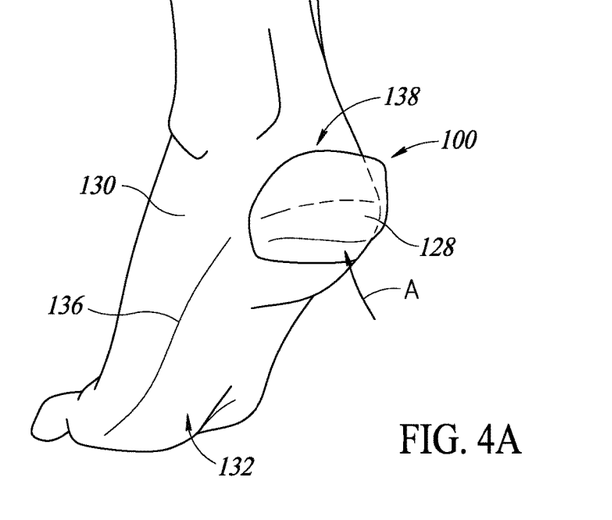
FIGS. 4A-4C are isometric views of process steps for applying the skin fissure mitigation device of FIG. 1 to the heel of the foot of the user.
Figure 4B:
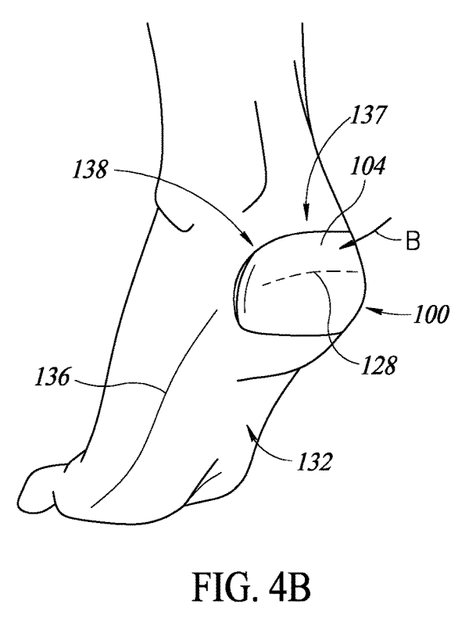
Figure 4C:
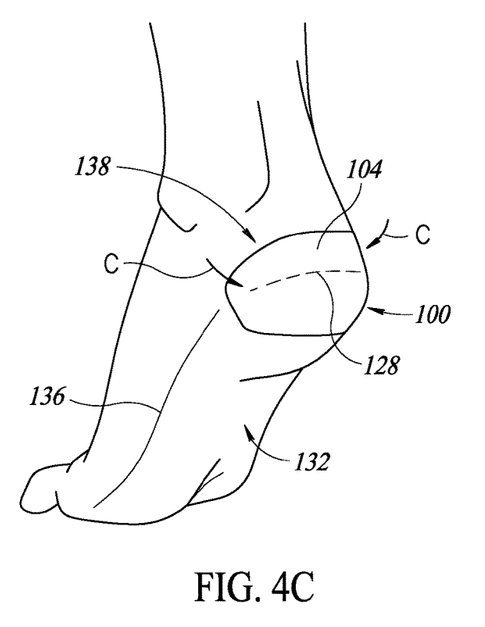

FIGS. 4A-4C are isometric views of process steps for applying the skin fissure mitigation device 100 to the heel 128 of the foot 130 of the user. Beginning with FIG. 4A, the user removes the cover layer 122 (FIG. 2) prior to application of the device 100 if a cover layer 122 (FIG. 2) is present. Then, the user first applies one side of the device 100 to the bottom surface 132 of the foot 130. Although FIG. 4A illustrates the device 100 applied first to the bottom surface 132 of the foot 130 with arrow A, the device 100 can also be applied first to the rear surface 137 of the foot 130 in some embodiments. When the user 100 applies the device 100 to the bottom surface 132 (or rear surface 137 of the foot 130 in an alternative embodiment), the user 100 also adheres a first adhesive, such as adhesive layer 120 (FIG. 2) on that portion of the device 100 to the foot 130.

Then, in FIG. 4B, the user pulls the sidewall 104 of the device 100 towards the rear surface 137 of the heel 128 of the user, (or towards the bottom surface 136 if the device 100 is attached to the rear surface 137 first), as indicated by arrow B. Pulling the sidewall 104 includes applying tension to the bottom surface 132 of the heel 128 and the heel 128 to close skin fissures in the bottom surface 132 of the foot 130. This process also applies tension to any cracks in the crown 136 of the foot proximate the heel 128 as well as cracks that may extend past the crown 136 towards the side surface 138. In other words, pulling the sidewall 104 of the device 100 may apply tension to the bottom surface 132, the crown 136, or the side surface 138, or any combination thereof, of the foot 130 of the user proximate the heel 128. Tension in any of these areas may assist with healing skin fissures, although it is believed that tension from pulling on the sidewall 104 at the side surface 138 of the foot 130 is most effective for healing. Once the sidewall 104 is in position, the user applies a second adhesive on a surface of the sidewall 104, such as adhesive 120 (FIG. 2), to the rear surface 137 of the foot 130 to attach the device 100 to the rear surface 137.

In FIG. 4C, the user pulls sides of the sidewall 104 towards the side surface 138 of the foot 130 and adheres a third adhesive, such as adhesive 120 (FIG. 2), on the sides of the sidewall 104 to the side surface 138 of the heel 128 of the user as indicated by arrows C. The process in FIG. 4C may also apply or increase tension in the device 100 by pulling the sides of the sidewall 104 away from the bottom surface 132 of the foot 130 and thus may assist with closing skin fissures in the heel 128. In some embodiments, the first, second, and third adhesives described with reference to FIGS. 4A-4C are the same adhesive layer positioned on different portions of the device 100 and may be the same as adhesive layer 120 shown in FIG. 2. The installation process is complete after the process shown and described with reference to FIG. 4C.

As described above, the device 100 is designed to be easy to apply and remove from the foot 130 of the user. The user can remove the device 100 after a selected period of time for healing, such as several days, weeks, or some other selected time. The user can also remove the device 100 and re-apply a second device 100 according to the same process if further treatment is needed or treatment is needed again after a certain time interval. In some embodiments, the device 100 is intended to be worn by a user for a period of one day, such that the process further includes repeating the steps above to remove and apply a new device 100 each day over a selected period of time, until the skin fissures completely heal. Frequent changing of the device 100 reduces the potential for bacterial growth in the device and thus reduces the risk of infection. Further, one or more embodiments of the device 100 include a medication, lotion, cream, gel, liquid, or other like product with disinfectant properties that is applied with the device 100 to further reduce the potential for infection and improve healing. The disinfectant may be a separate product applied with the device 100, or may be formed as a layer of the device 100 (i.e, as part of the adhesive layer 120 (FIG. 1) or a separate layer on the adhesive layer 120).

Figure 5A:
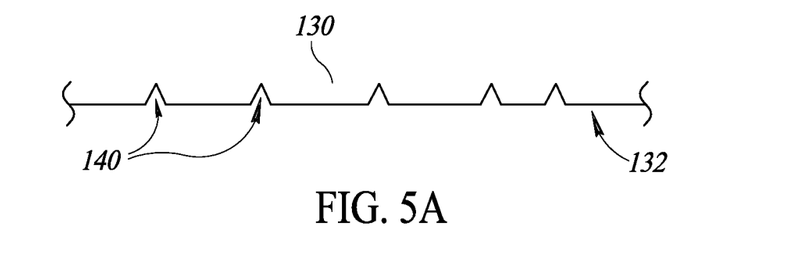
FIG. 5A and FIG. 5B are schematic views of the skin fissure mitigation device of FIG. 1 illustrating closing of skin fissures through tension in the skin fissure mitigation device.
Figure 5B:
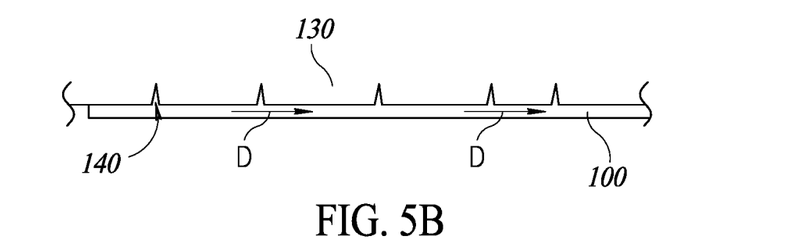

FIG. 5A and FIG. 5B are schematic detail views of the skin fissure mitigation device 100 that illustrate the closing of skin fissures through tension in the device 100. Specifically, FIG. 5A is a schematic view of the bottom surface 132 of the foot 130 of the user which may include cracks or skin fissures 140. The fissures 140 may also be on the crown 136 or side surface 138 or both, of the foot 130 as described herein with reference to FIGS. 3A-3C. In FIG. 5B, the device 100 is applied to the bottom surface 132 of the foot 130 according to the process described above with reference to FIGS. 4A-4C. The elastic material in some or all of the device 100 applies tension to the bottom surface 132 as indicated by arrows D. The tension in the device 100 closes the fissures and allows them to heal naturally. Further, the device 100 provides a barrier against further irritation or agitation to the fissures 140 and thus assist with the healing process in more ways than one. The same principles illustrated in FIG. 5B apply to skin fissures that may be on the crown 136 or side surface 138 (FIG. 3A) or both of the foot 130.

Figure 6:
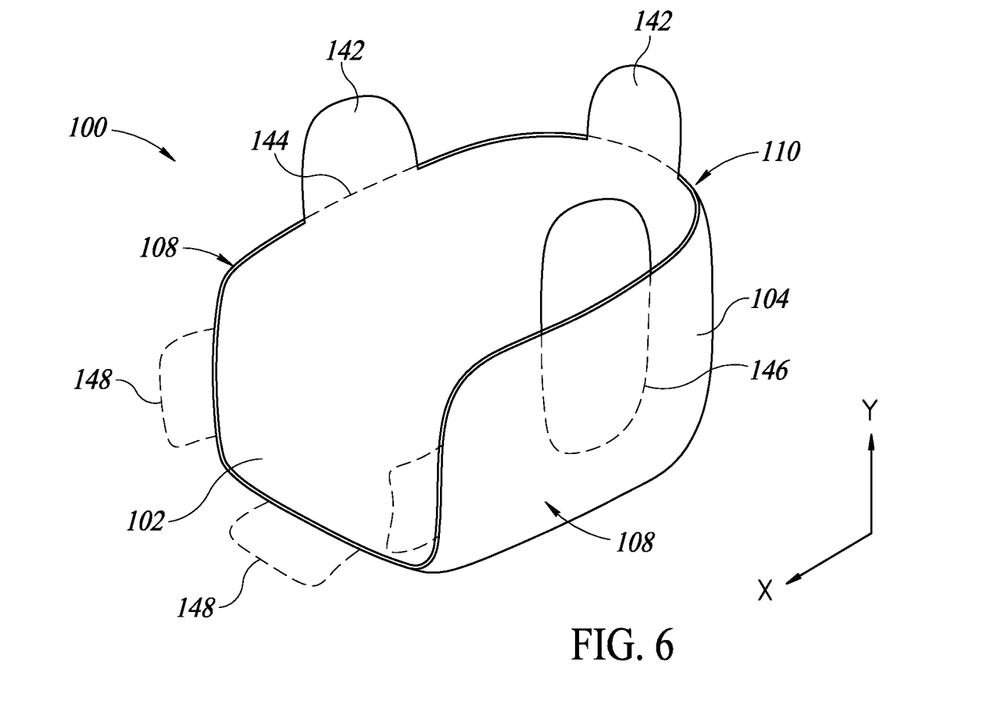
FIG. 6 is an isometric view of the skin fissure mitigation device of FIG. 1 with tabs to increase tension in the skin fissure mitigation device.

FIG. 6 is an isometric view of an additional embodiment of the skin fissure mitigation device 100. Specifically, the device 100 may include one or more first tabs 142 coupled to and extending from the device 100 to assist with installation or to apply additional tension to the skin fissures 140 (FIG. 5A), or both. The number, position, size, arrangement, and orientation of the first tabs 142 may be selected according to design factors and are not limited to the specific examples illustrated in FIG. 6. Thus, the device 100 may include more or less first tabs 142 with a different size or arrangement than those shown in FIG. 6.

The first tabs 142 may include at least three first tabs 142 coupled to the sidewall 104 of the device 100 and arranged equidistant from each other about the sidewall 104 as shown in FIG. 6. In some embodiments, the spacing between the first tabs 142 is different (i.e., not necessarily equidistant) and one or more of the first tabs 142 may have different spacing relative to the other first tabs 142. Each of the first tabs 142 in this embodiment may extend from the sidewall in a vertical or longitudinal direction indicated by axis Y in FIG. 6, although the same is not necessarily required. In one non-limiting example, the first tabs 142 may extend from the sidewall 142 at any angle between and including 0 and 90 degrees relative to axis Y. Further, the first tabs 142 may be formed as a single, unitary, integral component with the sidewall 104, as indicated by dashed lines 144 or may be a separate component coupled to the sidewall 104, as indicated by dashed lines 146.

In FIG. 6, the first tabs 142 include one tab 142 coupled to the curved portion 110 of the sidewall 104 and one tab 142 coupled to each of the opposing flat and planar portions 108 of the sidewall 104. In some embodiments, only one of the portions 108, 110 includes first tabs 142 or only two portions 108, 110 include first tabs 142. For example, the first tabs 142 may be only on the opposing flat and planar portions 108 or only on the curved portion 110, or on the curved portion 110 and only one of the opposing flat and planar portions 108. The first tabs 142 may also be located at an interface between the flat and planar portions 108 and the curved portion 110.

In some embodiments, the device 100 includes additional tabs represented by dashed lines 148 that are coupled to and extend from the front surface of the sidewall 104 and the base 102 (for ease of reference, the dashed lines 148 will be referred to as second tabs 148). The second tabs 148 may include at least one second tab 148 coupled to the sidewall 104 and extending from the sidewall 104 in a horizontal or lateral direction indicated by axis X in FIG. 6. Further, the second tabs 148 may include at least one second tab 148 coupled to and extending from the base 102 in the horizontal or lateral direction. The features of the first tabs 142 described above apply equally to the second tabs 148 and thus the number, size, spacing, arrangement, and orientation of the second tabs 148 are not necessarily limited to those shown in FIG. 6, but rather, include all of the variations described for the first tabs 142 in addition to others within the scope of the this disclosure.

In some embodiments, the first tabs 142 are identical to the second tabs 148 except for their position and orientation relative to the device 100 while in one or more embodiments, the first and second tabs 142, 148 are different because of design factors. In one non-limiting example, the first tabs 142 may be selected to be shorter than second tabs 148 to avoid the first tabs 142 from being visible while wearing socks and shoes. In an additional non-limiting example, the first tabs 142 may be selected to be longer than the second tabs 148 or at a different orientation relative to the device 100 in order to vary the tension on the foot 130 and increase adhesive between the first tabs 130 and the foot 130 (FIG. 3A) of the user. Further, all of the tabs 142, 148 may have the same construction or composition of materials as described with reference to the device 100 in FIG. 2.

Figure 7:
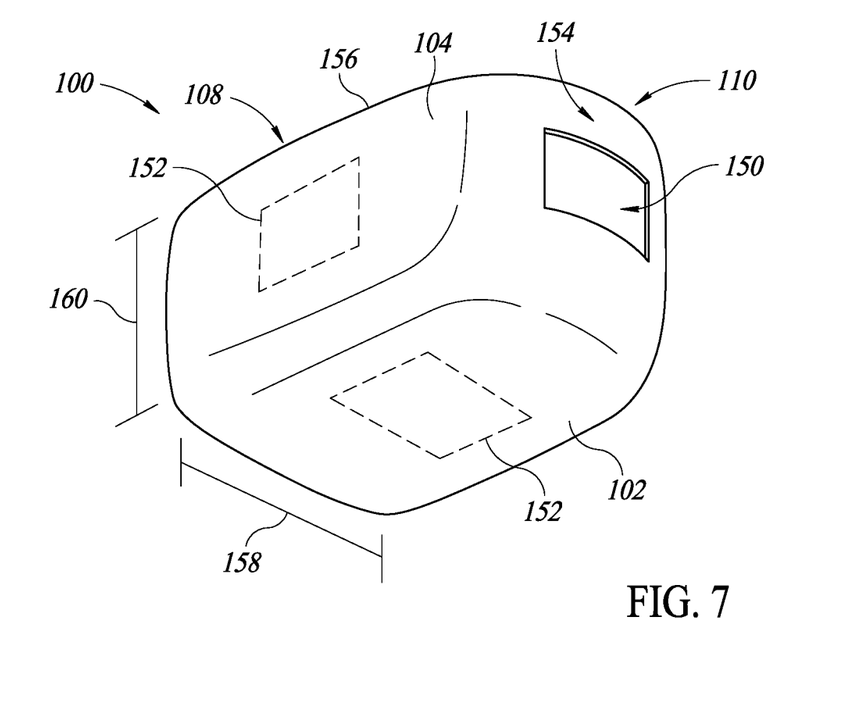
FIG. 7 is an isometric view of the skin fissure mitigation device of FIG. 1 with an opening in a sidewall to increase tension in the skin fissure mitigation device.

FIG. 7 is an isometric view of an additional embodiment of the skin fissure mitigation device 100. In FIG. 7, the skin fissure mitigation device 100 includes an opening 150 through the device 100 that acts similar to the tabs 142, 148 described above with reference to FIG. 6. More specifically, the opening 150 may be through the curved portion 110 of the sidewall 104 or through either or both of the flat and planar portions 108, or the base 102, or some combination thereof in some embodiments, as indicated by dashed lines 152. There may also be more than one opening 150 through any of the above areas of the device 100 in some embodiments. The opening 150 defines a tab portion 154 between an upper peripheral edge 156 of the sidewall 104 and the opening 150 that allows a user to more easily and effectively use the device 100 and apply tension to the fissures 140 (FIG. 5B) during installation. In other words, the user can grasp the tab portion 154 to pull against the base 102 installed on the user's foot to increase the tension in the device 100. Further, the tab portion 154 allows the user to more effectively manipulate the device 100 during installation by providing a structure for the user to grasp.

In some embodiments, the base 102 of the device 100 has a dimension 158, which may be a width, that is greater than a dimension 160 of the sidewall 104, which may be a height of the sidewall 104. The dimensions 156, 158 are equal in one or more embodiments, or the dimension 158 may be greater than the dimension 156. Further, the size and position of the opening 150 relative to the sidewall 104 or the base 102, or both, may be selected according to design factors. For example, the opening 150 may be located centrally on the sidewall 104 or the base 102 or the opening 150 may be located closer to the peripheral edge 156 or the base 102 when the opening is in the sidewall 104. Thus, the size or height of the tab portion 154 may also be selected and can vary in some embodiments. In some non-limiting examples, the height of the tab portion 154 may be any value less than 2 inches or less than 1 inch. Further, the size of the tab portion 154 and the opening 150 can be expressed as a fraction of the dimensions 158, 160. For example, the size of the opening may be 75%, 50%, 25% or more or less of the area of portions 108, 110 of the sidewall 104 or the base 102. Further, the tab portion 154 may have a height that is 25% or 15% or 10% or more or less than the dimension 160.

Figure 8:
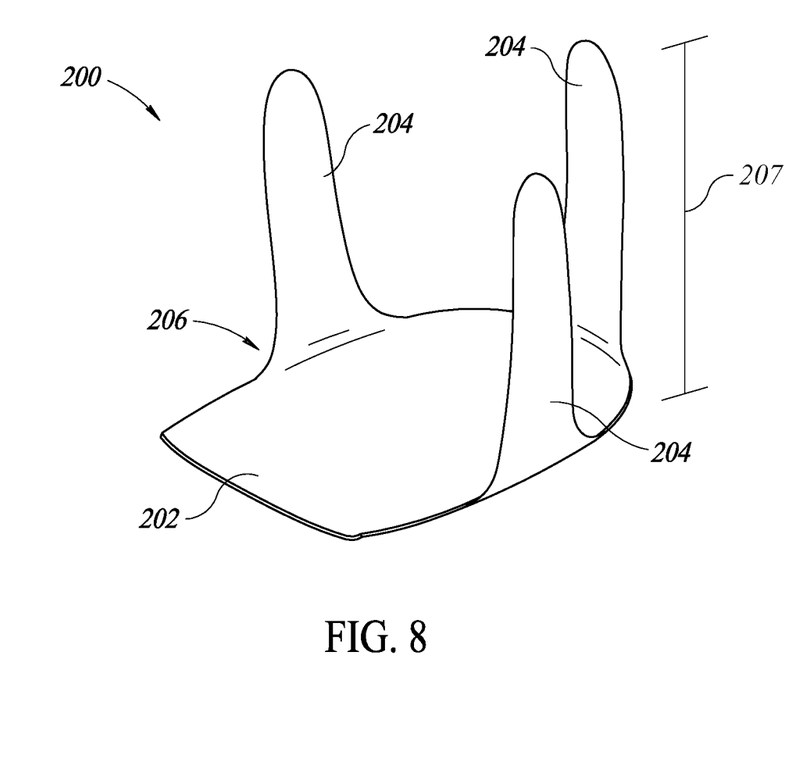
FIG. 8 is an isometric view of an embodiment of a skin fissure mitigation device with vertical tabs but no sidewalls according to the present disclosure.

FIG. 8 illustrates an embodiment of a skin fissure mitigation device 200 that may be similar to the device 100 except as otherwise described below. The device 200 includes a generally flat and planar base 202 that is structured to be adhered to the bottom surface of the heel of the foot of the user as described herein with reference to device 100. The device 200 replaces the sidewall around the base 202 with a plurality of tabs 204 coupled to the base 202. In some embodiments, the tabs 204 are integral with the base 202 as a single, unitary component. The tabs 204 may also include a transition portion 206 between the tabs 204 and the base 202 that is curved or continuously tapers in the unitary construction. In some embodiments, the tabs 204 are a separate component coupled to the base 202.

The tabs 204 may have a similar dimension 207 to the dimension 160 of the device 100 (FIG. 7) or the dimension 207 may be greater than or less than the dimension 160 (FIG. 7). Further, the tabs 204 may be spaced from each other about the base 202 by a selected distance that may be similar to the arrangement described above for tabs 142 in FIG. 6. The tabs 204 assist the user with installing the device 200 and also applying tension to the base 202 to close fissures in the bottom surface of the foot of the user. The device 200 may also include a collar or flange around the base 202 to assist with cracks that extend to the crown of the foot without including a sidewall similar to sidewall 104 (FIG. 6). Thus, a sidewall is not necessarily required for the devices described herein, but rather, the devices 100, 200 may include other structures for applying tension to the heel of the foot of the user.

Figure 9:
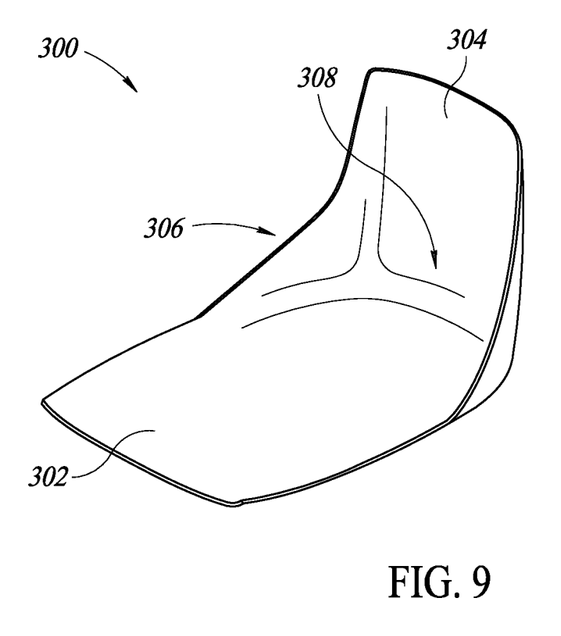
FIG. 9 is an isometric view of an embodiment of a skin fissure mitigation device with a rear wall but no sidewalls according to the present disclosure.

FIG. 9 illustrates an additional embodiment of a skin fissure mitigation device 300 that may be similar to devices 100, 200 except as otherwise described below. The device 300 includes a base 302 and a wall 304 coupled to the base 302. The wall 304 may be referred to herein as a sidewall 304, a heel wall 304, or a rear wall 304. The wall 304 is integrated with the base 302 as a single unitary component via transition portions 306 (which may also be referred to herein as flanges 306). The transition portions 306 may have a number of different configurations, such as curved, angled, tapered, step down, chamfered, or some other like transition between the substantially vertical wall 304 and the substantially horizontal base 302.

As shown in FIG. 9, the transition portions 306 are constantly tapered over at least a portion of, or all of, their length from the base 302 to the wall 304 in order to define, in combination with the base 302 and the wall 304, a cavity 308 for receiving the heel of the foot of the user. Thus, the device 300 does not include the flat and planar portions 108 of the sidewall 104 (FIG. 1) described above, but rather, includes a wall 304 with transition portions 306 to define a smaller cavity for receiving the heel of the foot of the user. Further, the device 300 is structured to apply tension only to a portion of a bottom surface of a foot of a user via base 302 and a portion of a rear surface of a heel of a foot of a user via rear wall 304. Despite the reduced wall area relative to device 100, the transition portions 306 of the device 300 assist with applying tension to heal skin fissures on the bottom surface of the foot as well as fissures that extend to the crown and the heel surface of the foot proximate the rear surface of the heel of the foot.

The wall 304 also increases tension in the base 302, similar to the tabs described herein, by providing a structure on which the user can pull to apply tension during installation. The device 300 has a reduced profile relative to device 100 such that the device 300 can be worn with a wider variety of footwear without being visible to external observers, such as low profile shoes or heels.

Certain words and phrases used in the specification are set forth as follows. As used throughout this document, including the claims, the singular form "a", "an", and "the" include plural references unless indicated otherwise. Any of the features and elements described herein may be singular, e.g., a sidewall may refer to one sidewall and a tab may refer to one tab. The terms "include" and "comprise," as well as derivatives thereof, mean inclusion without limitation. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. Other definitions of certain words and phrases are provided throughout this disclosure.

Throughout the specification, claims, and drawings, the following terms take the meaning explicitly associated herein, unless the context clearly dictates otherwise. The term "herein" refers to the specification, claims, and drawings associated with the current application. The phrases "in one embodiment," "in another embodiment," "in various embodiments," "in some embodiments," "in other embodiments," and other variations thereof refer to one or more features, structures, functions, limitations, or characteristics of the present disclosure, and are not limited to the same or different embodiments unless the context clearly dictates otherwise. As used herein, the term "or" is an inclusive "or" operator, and is equivalent to the phrases "A or B, or both" or "A or B or C, or any combination thereof," and lists with additional elements are similarly treated. The term "based on" is not exclusive and allows for being based on additional features, functions, aspects, or limitations not described, unless the context clearly dictates otherwise. In addition, throughout the specification, the meaning of "a," "an," and "the" include singular and plural references.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the present disclosure.

Generally, unless otherwise indicated, the materials for making the invention and/or its components may be selected from appropriate materials such as plastics, rubbers, thermoplastics, adhesives, tapes, polymers, and the like.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The foregoing description, for purposes of explanation, uses specific nomenclature and formula to provide a thorough understanding of the disclosed embodiments. It should be apparent to those of skill in the art that the specific details are not required in order to practice the invention. The embodiments have been chosen and described to best explain the principles of the disclosed embodiments and its practical application, thereby enabling others of skill in the art to utilize the disclosed embodiments, and various embodiments with various modifications as are suited to the particular use contemplated. Thus, the foregoing disclosure is not intended to be exhaustive or to limit the invention to the precise forms disclosed, and those of skill in the art recognize that many modifications and variations are possible in view of the above teachings.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the breadth and scope of a disclosed embodiment should not be limited by any of the above-described embodiments, but should be defined only in accordance with the following claims and their equivalents.

The invention claimed is:

1. A method for applying a skin fissure mitigation device to a bottom surface and a heel surface of a heel of a user, comprising:
    applying a base of the skin fissure mitigation device to the bottom surface of the heel of the user, including adhering a first adhesive on a surface of the base to the bottom surface of the heel of the user;
    pulling a sidewall of the skin fissure mitigation device towards the heel surface of the heel of the user, including applying tension to the bottom surface of the heel of the user to close skin fissures in the bottom surface of the heel of the user;
    adhering a second adhesive on a surface of the sidewall to the heel surface of the user;
    pulling sides of the sidewall towards the heel surface of the heel of the user; and
    adhering a third adhesive on the sides of the sidewall to the heel surface of the heel of the user.

2. The method of claim 1 wherein pulling sides of the sidewall includes pulling the sides of the sidewall away from the bottom surface of the heel of the user to apply tension to the heel of the user.

3. The method of claim 1 further comprising, before applying the base of the skin fissure mitigation device:
    removing a cover on the first adhesive, the second adhesive, and the third adhesive.

4. The method of claim 1, wherein the skin fissure mitigation device is an elastic material.

5. The method of claim 1, wherein the skin fissure mitigation device has a concave shape.

6. The method of claim 1, wherein the skin fissure mitigation device is a single, continuous, integral layer of material including the base and the sidewall.

7. A method for applying a skin fissure mitigation device to a first surface and a second surface of a heel of a user, comprising:
    applying a base of the skin fissure mitigation device to the first surface of the heel of the user, including adhering a first adhesive on a surface of the base to the first surface of the heel of the user;
    pulling a sidewall of the skin fissure mitigation device towards the second surface of the heel of the user, including applying tension to the first surface of the heel of the user to close skin fissures in the first surface of the heel of the user;
    adhering a second adhesive on a surface of the sidewall to the second surface of the heel of the user;
    pulling sides of the sidewall towards the second surface of the heel of the user; and
    adhering a third adhesive on the sides of the sidewall to the second surface of the heel of the user.

8. The method of claim 7 wherein pulling sides of the sidewall includes pulling the sides of the sidewall away from the first surface of the heel of the user.

9. The method of claim 7 further comprising, before applying the base of the skin fissure mitigation device:
    removing a cover on at least one of the first adhesive, the second adhesive, and the third adhesive.

10. The method of claim 7, wherein the first surface is a bottom surface of the heel of the user.

11. The method of claim 7, wherein the second surface is a heel surface of the heel of the user.

12. The method of claim 7, wherein the first surface is a bottom surface of the heel of the user and the second surface is a heel surface of the heel of the user.

* * * * *